United States Patent [19]

Henne et al.

[11] Patent Number: 4,719,297

[45] Date of Patent: Jan. 12, 1988

[54] ACYLPHOSPHINE COMPOUNDS AND THEIR USE AS PHOTOINITIATORS

[75] Inventors: Andreas Henne, Ludwigshafen; Anton Hesse, Weinheim; Manfred Jacobi, Frankenthal; Guenter Wallbillich, Schifferstadt; Bernd Bronstert, Otterstadt, all of Fed. Rep. of Germany

[73] Assignee: BASF Aktiengesellschaft, Ludwigshafen, Fed. Rep. of Germany

[21] Appl. No.: 673,218

[22] Filed: Nov. 20, 1984

Related U.S. Application Data

[63] Continuation of Ser. No. 365,965, Apr. 6, 1982, abandoned.

[30] Foreign Application Priority Data

Apr. 8, 1981 [DE] Fed. Rep. of Germany ....... 3114341

[51] Int. Cl.$^4$ ............................ C07F 9/32; C07F 9/40; C07F 9/65
[52] U.S. Cl. ................................... 544/107; 544/108; 544/109; 544/110; 558/70; 260/501.21; 260/502.4 R; 260/502.5 R; 546/22
[58] Field of Search ...... 260/501.21, 502.4 R, 502.5 R; 558/70; 544/108, 107, 110

[56] References Cited

U.S. PATENT DOCUMENTS 4,257,859 3/1981 Fischer et al. ................. 204/159.23
4,265,723 5/1981 Hesse et al. ................... 204/159.23

FOREIGN PATENT DOCUMENTS 0009348 4/1980 European Pat. Off. .

Primary Examiner—Alan L. Rotman
Attorney, Agent, or Firm—Keil & Weinkauf

[57] ABSTRACT

Acylphosphine compounds of the formula I

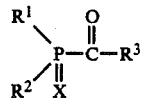

where X is oxygen, sulfur or an electron pair, $R^1$ is $R_4$ or $OR^4$, $R^2$ is —OM, where M is a monovalent cation, $R^3$ is aryl which is substituted at least at the two positions ortho to the carbonyl group, and $R^4$ is hydrogen, alkyl or aryl, are very effective photoinitiators for photopolymerizable materials, such as coating compositions, finishes, printing inks, unsaturated polyesters, recording media and preferably aqueous polymer dispersions or solutions.

6 Claims, No Drawings

ACYLPHOSPHINE COMPOUNDS AND THEIR USE AS PHOTOINITIATORS

This application is a continuation of application Ser. No. 365,965, filed on Apr. 6, 1982, abandoned.

The present invention relates to novel acylphosphine compounds and their use as photoinitiators in polymerizable materials, such as coating compositions, finishes, printing inks, unsaturated polyester molding compositions and recording media, and in photopolymerizable aqueous mixtures, such as aqueous polymer dispersions or polymer solutions.

A number of photoinitiators of various structures are known, examples being benzil ketals, benzoin ethers and thioxanthone. However, photopolymerizable materials which have been hardened using initiator systems of these types exhibit undesirable yellowing, which makes the systems unsuitable for use on pale surfaces, or for hardening translucent moldings. A further disadvantage of the above classes of compounds, and of the acylphosphine oxides used as photoinitiators and described in U.S. Pat. No. 4,265,723, is that the shelf life of the ready-sensitized resin mixtures is inadequate in many cases so that many of the mixtures can be kept for only a few days, even when stored in the dark. Moreover, there is a need for initiators which are more active hardeners than the above classes of compounds.

Photoinitiators with a water-solubility of about 1–3% are required for the photopolymerization of aqueous mixtures, and examples of such compounds are the benzoin derivatives containing a quaternary ammonium group which are described in U.S. Pat. No. 4,257,859. However, there is still a need for water-soluble photoinitiators which absorb light of longer wavelength and are more active than the compounds described in the above publication.

It is an object of the present invention to provide compounds which absorb light of longer wavelength than do the compounds disclosed in U.S. Pat. No. 4,257,859, and thus may be hardened using less dangerous light sources or using sunlight. A further object of the invention is to provide compounds which are more active hardeners than the acylphosphine oxides disclosed in U.S. Pat. No. 4,265,723 and make it possible to obtain ready-sensitized resin mixtures with a longer shelf life.

We have found that this object is achieved by acylphosphine compounds of the general formula (I)

The present invention also relates to the use of acylphosphine compounds of the general formula I as photoinitiators in photopolymerizable materials, for example coating compositions, finishes, printing inks and recording media, in molding compositions based on unsaturated polyester resins, and for the photopolymerization of aqueous solutions, dispersions and emulsions.

Acylphosphine oxide compounds of a similar type, their preparation and their use as plant treatment agents have been claimed in European Published Application No. 9,348, but this does not describe any of the compounds of the present invention which contain the special arrangement of substituents in $R_3$, nor does it indicate that the compounds it describes may be used as photoinitiators.

In respect of the general formula I of the novel acylphosphine compounds, the following specific meanings may be listed:

$R^3$ is preferably a phenyl radical which is substituted at least at the two positions ortho to the carbonyl group, and may also be a correspondingly substituted naphthyl, furyl, thienyl, pyrrolyl or pyridyl radical. $R^3$ is preferably 2,6-dimethylphenyl, 2,6-dimethoxyphenyl, 2,6-dichlorophenyl, 2,6-dibromophenyl, 2-chloro-6-methoxyphenyl, 2-chloro-6-methylthiophenyl, 2,4,6-trimethylphenyl, 2,4,6-trimethoxyphenyl, 2,3,5,6-tetramethylphenyl, 2,6-dimethyl-4-tert.-butylphenyl, 1,3-dimethylnaphth-2-yl, 2,8-dimethylnaphth-1-yl, 1,3-dimethoxynaphth-2-yl, 1,3-dichloronaphth-2-yl, 2,8-dimethoxynaphth-1-yl, 2,4,6-trimethylpyrid-3-yl, 2,4-dimethoxyfur-3-yl or 2,4,5-trimethylthien-3-yl.

X may be oxygen, sulfur or a free electron pair on the phosphorus atom, but is preferably oxygen, and $R^2$ is $-O^-M^\oplus$ or $-NR^5R^6$.

$M^\oplus$ is one equivalent of a cation of main groups 1 to 3 of the Periodic Table, eg. a hydrogen, lithium, sodium, potassium, magnesium, calcium, barium or aluminum ion or an ammonium ion of the general formula

$N^\oplus R^5 R^6 R^7 R^8$ (II)

or

(II')

Examples of such ammonium ions are ammonium, triethylammonium, tributylammonium, tetramethylammonium, tetraethylammonium, methyldiethanolammonium, anilinium, N,N-dimethylanilinium, β-acryloxyethyldiethylammonium, β-acryloxyethyldiethylammonium and N-(β-hydroxyethyl)morpholinium, and the divalent 1,4-diazabicyclo-[2.2.2]-octane dication (II').

Examples of $R^1$ are hydrogen, methyl, ethyl, isopropyl, n-butyl, sec.-butyl, isobutyl, t-butyl, amyl, n-hexyl, vinyl, 2-methylvinyl, prop-2-enyl, 2-dimethylaminoethyl, 3-dimethylaminopropyl, cyclohexyl, cyclopentyl, phenyl, halogen-substituted phenyl, eg. monochlorophenyl or dichlorophenyl, $C_1$–$C_4$-alkyl-substituted phenyl, eg. methylphenyl, ethylphenyl, isopropylphenyl, tert.-butylphenyl, dimethylphenyl and trimethylphenyl, and $C_1$–$C_4$-alkoxy-substituted phenyl, eg. methoxyphenyl, ethoxyphenyl and dimethoxyphenyl.

Examples of preferred acylphosphine compounds are monomethyl 2,4,6-trimethylbenzoylphosphinate, 2,4,6-trimethylbenzoylphosphinic acid, 2,6-dimethoxybenzoylmethylphosphinic acid and 2,4,6-trimethylbenzoyl-n-butylphosphinic acid, and the salts of these acids with the above cations.

Examples of particularly preferred compounds are 2,4,6-trimethylbenzoylphosphinic acid and its Li, Na, K, Ca, Ba, Mg, Al, triethylammonium, methyldiethanolammonium, tributylammonium, β-acryloxyethyldiethylammonium, anilinium, dimethylanilinium and 1,4-diazobicyclo-[2.2.2]-octane salts, 2,4,6-trimethylbenzoyl-o-tolylphosphinic acid, 2,4,6-trimethylbenzoyl-p-tolylphosphinic acid, 2,6-dimethoxybenzoylphenylphosphinic acid, 2,6-dichlorobenzoylphenylphosphinic acid and 2,6-dimethylbenzoylphenylphosphinic acid, and the salts of these acids with the above cations, and 2,6-dimethoxybenzoylphenylphosphinic acid dimethylamide.

In one of the processes for the preparation of the novel compounds, an acylphosphine compound of the general formula (III) is reacted with a metal halide $M^{\oplus}Y^{\ominus}$ in a polar solvent at from 0° to 150° C.

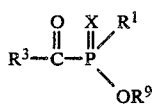
(III)

In this formula, $R^1$, $R^3$, $M^{\oplus}$ and X have the above meanings, $R^9$ is branched or straight-chain alkyl of 1 to 6 carbon atoms, preferably methyl, and Y is a fluoride, chloride or bromide ion but preferably an iodide ion. Suitable polar solvents are alcohols, eg. methanol and ethanol, nitriles, eg. acetonitrile and benzonitrile, sulfoxides, eg. dimethylsulfoxide, tetramethylenesulfone, and ethers, eg. tetrahydrofuran, and, preferably, ketones, eg. acetone and methyl ethyl ketone. The solvent may contain up to 0.2 mole of a phase transfer catalyst or of a crown ether per mole of the metal halide MX in order to increase the solubility of the latter.

In a preferred embodiment of the reaction, the salt MY and the phosphine compound of the formula (III) are dissolved in the solvent. The acylphosphine compound of the formula (I) is precipitated immediately or after heating, and may be filtered off and, if required, purified further by processes known to a skilled worker.

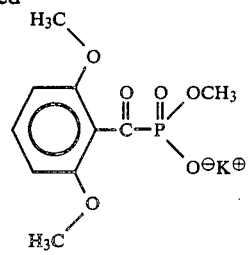

The starting compound of the general formula (III) is obtainable, for example, by the procedure described in U.S. Pat. No. 4,265,723 (if $R^1=R^4$), or by a conventional route (if $R^1=OR^4$; see R. S. Marmor and D. Seyferth, J. Org. Chem. 36 (1971), 128). Compounds of the general formula (III) where $R^9$ is methyl are preferably used, since they react particularly rapidly with the metal halide MY.

In another process for the preparation of the compound of the general formula (I), a metal salt of the formula (IV)

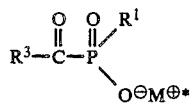
(IV)

is reacted with a metal salt of the formula $M^{\oplus}Z^{\ominus}$ in a polar solvent to give the desired metal salt of the formula (I). In these formulae, $R^1$, $R^3$ and $M^{\oplus}$ have the above meanings, $M^{\oplus *}$ has the same meanings as $M^{\oplus}$, $Z^{\ominus}$ is one equivalent of any desired anion. Suitable polar solvents for the reaction are those given above, but water is preferred. This process is preferably used when the salt of the formula (IV) and the salts $M^{\oplus}Z^{\ominus}$ and $M^{\oplus *}Z^{\ominus}$ are readily soluble in the chosen solvent, but the desired salt of the formula (I) is only sparingly soluble therein. The latter salt is then precipitated when the solutions of $M^{\oplus}Z^{\ominus}$ and of the salt of the formula (IV) are combined, and may be purified further, if required, by processes known to the skilled worker.

This process may be represented by, for example, the following equations:

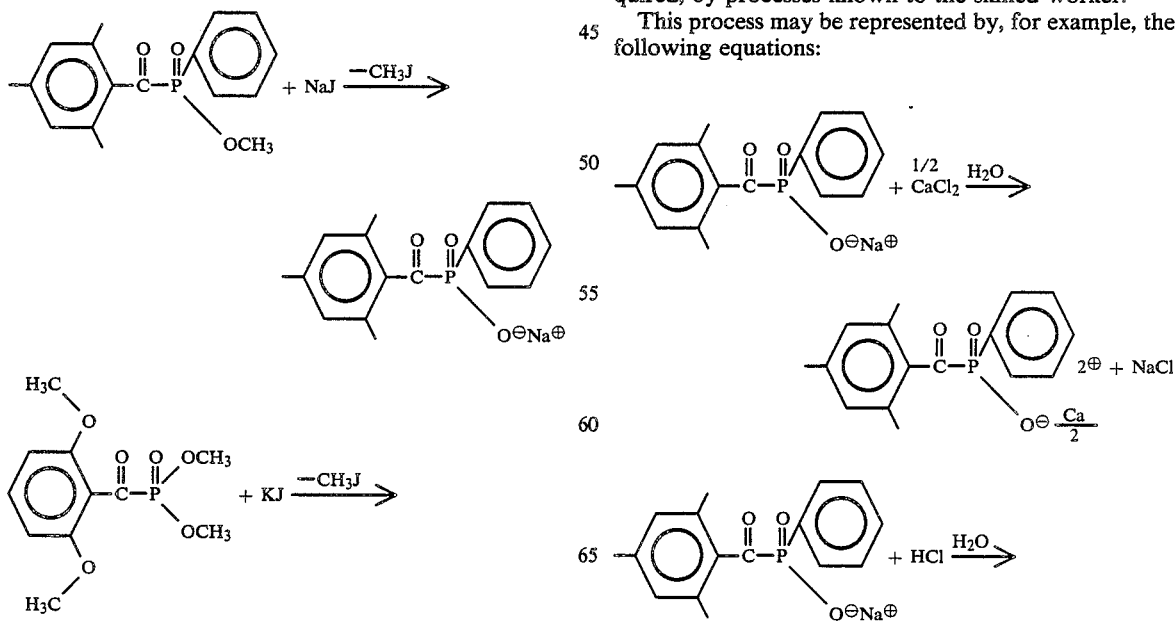

-continued

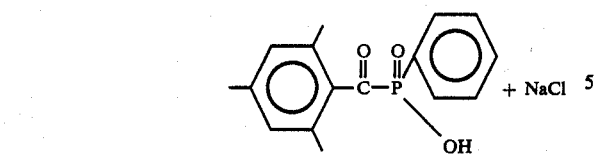 + NaCl

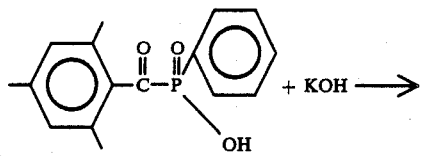 + KOH →

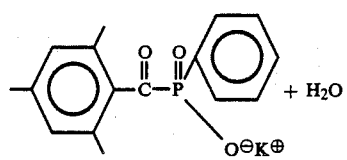 + H₂O

A third process gives the ammonium salts of the formula (I) when a phosphinic acid or a phosphonic acid ester of the formula (V)

$$R^3-\overset{O}{\underset{}{C}}-\overset{X}{\underset{OH}{P}}\overset{R^1}{}$$ (V)

is reacted with a stoichiometric amount of an amine of the formula (VI)

NR⁵R⁶R⁷ (VI)

where R¹, R³, X, R⁵, R⁶ and R⁷ have the above meanings, at from 0° to 100° C., either in the absence of a solvent or in the presence of a polar or non-polar solvent, eg. methanol, acetone, methylene chloride, toluene, acetonitrile or tetrahydrofuran, and the solvent is subsequently distilled off.

The following examples illustrate this reaction:

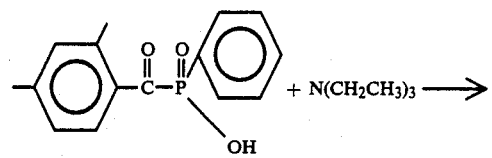 + N(CH₂CH₃)₃ →

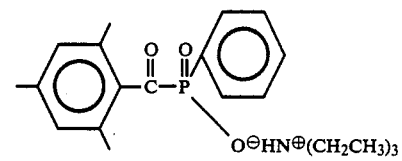

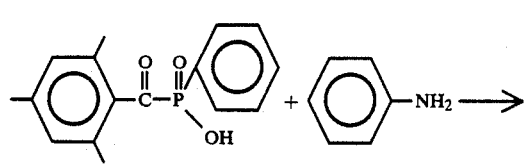 + 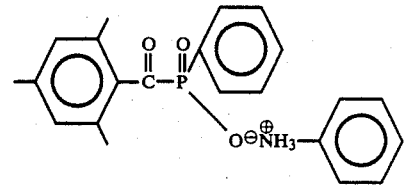

Examples of the novel compounds are, in particular, those listed in Table 1 and of the general formula (I) where X is 0, but the invention is not restricted to these examples.

TABLE 1

| No. | Compound (Ph = phenyl) R³ | R¹ | R² | Preparation process | Yield in % | Analysis | | | | |
|---|---|---|---|---|---|---|---|---|---|---|
| | | | | | | C | H | P | M | mp. |
| 1 | 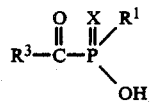 | CH₃ | OCH₃ | ONa | I | 94 | calc. 50.0 found 47.0 | 5.3 5.4 | 11.7 11.2 | 8.71 8.3 | >280° |
| 2 | " | OCH₃ | OH | II from Compound 1 | | calc. found | | | | 303–306° |
| 3 | " | OCH₃ | OLi | I | 95 | calc. 53.23 found 48.9 | 5.65 5.9 | 12.5 12.2 | 2.82 n.b. | >270° |
| 4 | " | Ph | ONa | I | 100 | calc. 61.9 found 60.7 | 5.2 5.4 | 10.0 9.8 | 7.4 7.5 | >300° |
| 5 | " | Ph | OLi | I | 97 | calc. 65.3 found 63.8 | 5.44 5.5 | 10.54 10.3 | 2.38 n.b. | >340° |
| 6 | " | Ph | OK | II from Compound 10 | 90 | calc. 58.9 found 58.0 | 4.91 5.0 | 9.51 9.3 | 11.96 11.2 | 305–308° |
| 7 | " | Ph | OMg | II from Compound 10 | 82 | calc. 64.21 found 63.3 | 5.35 5.4 | 10.37 10.1 | 4.01 n.b. | not determined |
| 8 | " | Ph | OCa | II from Compound 4 | 100 | calc. 62.54 found 57.1 | 5.21 5.3 | 10.10 9.9 | 6.51 n.b. | 335° |
| 9 | " | Ph | OBa | II from Compound 4 | 86 | calc. 54.01 found 52.4 | 4.50 4.7 | 8.72 5.7 | 19.27 n.b. | >310° |

TABLE 1-continued

| No. | Compound (Ph = phenyl) R³ | R¹ | R² | Preparation process | Yield in % | Analysis | | | | | |
|---|---|---|---|---|---|---|---|---|---|---|---|
| | | | | | | | C | H | P | M | mp. |
| 10 | " | Ph | OH | II from Compound 4 | 90 | calc. found | 66.67 66.7 | 5.9 6.0 | 10.76 10.8 | | 146–9° |
| 11 | " | Ph | O⁻ ⁺NHEt₃ | III | 100 | calc. found | | | | | |
| 12 | " | Ph | O⁻HN⁺CH₃(CH₂CH₂OH)₂ | III | 100 | calc. found | 61.92 61.7 | 7.37 7.3 | 7.62 7.4 | | 84–89° |
| 13 | " | Ph | O⁻HPhN⁺(CH₂CH₃)₂ | III | 100 | calc. found | 71.42 70.2 | 7.32 7.2 | 7.09 7.3 | | <20° |
| 14 | " | Ph | O⁻HN⁺(n-Bu)(CH₂CH₂OH)₂ | III | 100 | calc. found | 64.14 63.5 | 8.02 8.0 | 6.90 6.5 | | 78–83° |
| 15 | " | Ph | O⁻NH₃⁺Ph | III | 100 | calc. found | 69.29 68.6 | 8.14 6.2 | 8.14 7.4 | | 167–8° |
| 16 | " | Ph | O⁻HN⁺Ph(CH₃)₂ | III | 100 | calc. found | 70.42 69.8 | 6.85 6.9 | 7.58 8.0 | | <20° |
| 17 | " | Ph | O⁻HN⟨ring⟩⁺NH/2 | III | 95 | calc. found | 66.28 65.4 | 6.69 6.7 | 9.01 8.8 | | 154° |
| 18 | " | Ph | (CH₃CH₂)₂N⁺H—(CH₂)₂—O—C(=O)—CH=CH₂ | III | 95 | | | | | | 20° |
| 19 | " | Ph | N(CH₂—CH₂)₂ | | | calc. found | 69.97 69.8 | 7.58 7.6 | 9.04 9.0 | | 76–79° |
| 20 | " | Ph | NH—Ph | | | calc. found | 72.7 72.5 | 6.06 6.2 | 8.54 8.8 | | 157–159° |

The novel acylphosphine compounds are suitable as photoinitiators for the photopolymerization of polymerizable mixtures containing olefinically unsaturated compounds, particularly of mixtures which contain water as the solvent or diluent.

They are suitable, for example, for the photopolymerization of printing plates based on partially or completely hydrolyzed polyvinyl acetate or polyamides, the differentiation of the image obtained being adequate for reproduction purposes. They are also suitable for the photopolymerization of aqueous emulsions or solutions of olefinically unsaturated monomers, or of monomer mixtures obtained from such emulsions or solutions. In this manner, aqueous polymer dispersions or aqueous polymer solutions which may be used in industry are obtained in an acceptable time and with high conversion.

Stable aqueous polymer dispersions with high solids contents may be obtained by the action of UV light on aqueous emulsions of olefinically unsaturated monomers in the presence of emulsifiers and/or protective colloids and of the novel compounds as photoinitiators.

A high molecular weight solution polymer with a small residual amount of monomers may likewise be obtained by exposing an aqueous solution of olefinically unsaturated monomers to UV light in the presence of a novel acylphosphine compound.

With the novel photoinitiators, conversions of from 98 to 100% are achieved, without the additional use of peroxides or redox initiators. The polymer solutions are homogeneous and show no discoloration.

All conventional solvents, such as dimethylformamide, acetone, tetrahydrofuran, hydrocarbons, alcohols, acetic acid esters, etc., but preferably water, are suitable for use, according to the invention, as initiators for the preparation of aqueous polymer solutions or emulsions, or of mixtures obtained therefrom.

When used for hardening aqueous polymer solutions or emulsions, or mixtures obtained therefrom, the novel photoinitiators are substantially more active hardeners than the prior art compounds described in U.S. Pat. No. 4,257,859. Moreover, time-consuming pre-exposure of the monomer solutions or emulsions, or of the mixtures obtained therefrom, is required in many cases before photopolymerization using the compounds described in U.S. Pat. No. 4,257,859, whereas, with the more active compounds of the present invention, this operation may be dispensed with.

The novel acylphosphine compounds are also very suitable for use as photoinitiators in photopolymerizable materials for coatings, finishes, printing inks and recording media, and are far superior to conventional photoinitiators, eg. benzil dimethyl ketal, in respect of yellowing of the finishes or coatings thus obtained. Futhermore, finishes may be hardened more rapidly using the novel compounds than with benzil dimethyl ketal or with the acylphosphine oxides disclosed in U.S. Pat. No. 4,265,723. Finally, the resins containing the novel compounds have longer shelf lives than those which contain the acylphosphine oxides described in U.S. Pat. No. 4,265,723, as photoinitiators. The novel compounds are therefore very advantageously used for the photohardening of a solution of a polyester in styrene, with or without glass fibers, fillers and other assistants.

Suitable olefinically unsaturated photopolymerizable compounds are the conventional monomers, for example monoolefins and diolefins, eg. ethylene, butadiene, isoprene and chloroprene, olefinically unsaturated carboxylic acid esters, such as acrylates and methacrylates of alcohols of 1 to 12 carbon atoms, or vinyl esters of fatty acids of 2 to 20 carbon atoms, vinyl halides and vinylidene halides, particularly vinyl chloride and vinylidene chloride, aromatic vinyl compounds, eg. styrene, α-methylstyrene and vinyltoluenes, and mixtures of monomers of this type with one another and with α,β-olefinically unsaturated monocarboxylic acids and dicarboxylic acids, particularly acrylic acid, methacrylic acid, maleic acid, fumaric acid and itaconic acid, and their amides, N-methylolamides, N-alkoxymethylamides and nitriles, in particularly acrylamide, methacrylamide, maleimide, itaconic acid diamide, N-methylolmethacrylamide, N-methylolacrylamide, N-methoxymethylacrylamide, N-n-butoxymethylacrylamide, N-methoxymethylmethacrylamide, methylene-bis-acrylamide, acrylonitrile and methacrylonitrile.

Examples of ethylenically unsaturated carboxylic acid esters particularly suitable for use in the polymers are methyl acrylate, ethyl acrylate, ethyl methacrylate, isopropyl acrylate, n-butyl acrylate, isobutyl acrylate, tert.-butyl acrylate, 2-ethylhexyl acrylate, 2-ethylhexyl methacrylate, 2-hydroxyethyl acrylate, 2-hydroxyethyl methacrylate, hydroxypropyl acrylate, hydroxypropyl methacrylate, acrylates and methacrylates of dihydric and polyhydric alcohols, eg. ethylene glycol diacrylate, butanediol-1,4-dimethacrylate and 1,1,1-trimethylolpropane triacrylate, acrylates and methacrylates of dialcohols of the formula $HO(CH_2-CH_2O)_n$ where n is 2-20, vinyl acetate, vinyl propionate, vinyl laurate, vinyl stearate and vinyl esters of branched saturated carboxylic acids, eg. of pivalic acid.

Particularly useful aqueous polymer dispersions are those which contain polymers or copolymers derived from acrylates and/or methacrylates of alkanols of 1 to 8 carbon atoms, and/or from vinyl esters of saturated monocarboxylic acids of 2 to 12 carbon atoms, or from mixtures of butadiene with styrene and/or acrylonitrile, and which preferably contain from 0.5 to 5% by weight, based on the polymer, of α,β-olefinically unsaturated carboxylic acids of 3 to 5 carbon atoms and of the above type as copolymerized units.

Aqueous polymer solutions which contain polymers or copolymers of acrylic acid, methacrylic acid, acrylamide, methacrylamide, N-alkanolamides of acrylic and/or methacrylic acid, and/or water-soluble hydroxyalkyl acrylates are also of particular interest.

In general, ionic and/or non-ionic emulsifiers, such as polyglycol ethers, sulfonated paraffin hydrocarbons, higher alkyl sulfates, eg. lauryl sulfate, alkali metal salts of fatty acids, eg. sodium stearate and sodium oleate, sulfates of fatty alcohols, oxyethylated $C_8$-$C_{12}$-alkylphenols containing from 5 to 30 ethylene oxide residues in most cases, and the sulfonation products thereof, and sulfosuccinic acid esters, are employed, in most cases in amounts of from 0.1 to 10.0% by weight, based on the monomers, for the novel preparation of aqueous polymer dispersions. In some cases a protective colloid is also present, and examples of suitable ones are polyvinyl alcohol, partially hydrolyzed polyvinyl acetates, cellulose derivatives, copolymers of methyl acrylate with acrylamide and methacrylamide, and vinylpyrrolidone polymers, used in amounts of about 0.5-10, in particular 1.0-5, % by weight, based on the monomers.

The novel photoinitiators are employed in concentrations of from 0.001 to 10% by weight, preferably from 0.01 to 1% by weight, based on the olefinically unsaturated compounds. In this concentration range, the photo-initiators are dissolved completely by water. If required, they may be combined with accelerators which eliminate the inhibiting effect of atmospheric oxygen on the photopolymerization.

The photopolymerization of aqueous solutions or emulsions using the novel photoinitiators may be carried out either batchwise or continuously. The individual components are emulsified or dissolved by known processes, and these emulsions or solutions are then exposed to light. The heat of polymerization may be removed by external cooling or by evaporative cooling. The exposure time depends on the type of procedure, on the type and concentration of the monomers employed, on the type and amount of photoinitiators employed, on the intensity of the light source and on the size of the mixture, and may be from 5 minutes to 4 hours, preferably from 10 minutes to 3 hours. The polymerization may be carried out at from +5° to about 100° C., the choice of temperature being unrestricted within this range, but is particularly preferably carried out at from 10° to 40° C. The solids contents of the dispersions prepared according to the invention are from 5 to 60% by weight, preferably from 30 to 50% by weight, and the content of residual monomers is low. The Fikentscher K values of the dispersions obtained are high, and are in general >90.

Apart from the above compounds, higher molecular weight compounds, such as unsaturated polyesters prepared by reacting α,β-unsaturated dicarboxylic acids, eg. maleic acid, furmaric acid or itaconic acid, if required mixed with saturated or aromatic dicarboxylic acids, eg. adipic acid, phthalic acid or terephthalic acid, with alkanediols, eg. ethylene glycol, propylene glycol, butanediol, neopentyl glycol or oxyalkylated bisphenol A, or such as epoxide acrylates prepared from acrylic acid or methacrylic acid and aromatic or aliphatic diglycidyl ethers, or such as urethane acrylates prepared from hydroxyalkyl acrylates and polyisocyanates, and polyester acrylates prepared from hydroxyl-containing saturated polyesters and acrylic acid or methacrylic acid, are also suitable for the production of photopolymerizable materials, finishes, coatings, unsaturated polyester resin molding compositions, printing inks and recording media.

Saturated and/or unsaturated polymers, and other additives, such as thermal polymerization inhibitors, paraffin, pigments, dyes, peroxides, leveling agents, fillers and glass fibers, and stabilizers to thermal or photochemical degradation may be added in a conventional manner to the photopolymerizable compound, whose composition for the particular intended use is well known to the skilled worker.

Examples of suitable accelerators and synergists are secondary and tertiary amines, eg. methyldiethanolamine, dimethylethanolamine, triethylamine, triethanolamine, ethyl p-dimethylaminobenzoate, benzyldimethylamine, dimethylaminoethyl acrylate, N-phenylglycine and N-methyl-N-phenylglycine. The hardening process may also be accelerated by using aliphatic and aromatic halides, eg. 2-chloromethylnaphthalene or 1-chloro-2-chloromethylnaphthalene, in the presence or absence of radical formers, as employed in general as initiators for thermal polymerization, eg. peroxides, azo compounds and stable C—C-labile compounds, in amounts of up to 15% by weight, based on the photopolymerizable material.

Furthermore, the acylphosphine compound may be employed together with other photoinitiators, in the presence or absence of the above synergists and accelerators, for the photohardening of coatings, finishes, printing inks, photosensitive recording media, eg. photopolymerizable printing plates, and styrene-based polyester resins. Examples of such photoinitiators are aromatic ketones, such as benzil ketals, and benzoin ethers, benzoin esters, $C_1$-$C_3$-alkyl-substituted, chlorine-substituted or chloromethyl-substituted thioxanthones, the acylphosphine oxides and acylphosphinic acid esters disclosed in U.S. Pat. No. 4,265,723, aromatic disulfides, and naphthalenesulfonyl chlorides.

The radiation source used for initiating the polymerization of such mixtures is in general one which emits light preferably in the absorption range of the novel compounds, ie. 230–450 nm. Low, medium and high pressure mercury vapor lamps, superactinic fluorescent tubes and pulsed discharge lamps are particularly suitable, and these lamps may or may not be doped.

In the Examples which follow, parts and percentages are by weight, unless stated otherwise. Parts by volume bear the same relation to parts by weight as that of the liter to the kilogram.

EXAMPLE 1

Sodium 2,4,6-trimethylbenzoylphenylphosphinate (Compound 4)

60.5 parts by weight of methyl 2,4,6-trimethylbenzoylphenylphosphinate (as described in U.S. Pat. No. 4,265,723) and 33 parts by weight of sodium iodide were dissolved in 560 parts by volume of methyl ethyl ketone, and the solution was stirred for 2.5 hours at 55° C. The resulting precipitate was filtered off, washed with methyl ethyl ketone and dried, the desired product being obtained.

EXAMPLE 2

2,4,6-Trimethylbenzoylphenylphosphinic acid (Compound 10)

46.5 parts by weight of the sodium salt of Example 1 were dissolved in 300 parts by weight of water, and 150 parts by volume of 1N sulfuric acid were added. The resulting precipitate was filtered off under suction, washed with water and dried, and 38.9 parts by weight of product were obtained.

EXAMPLE 3

Calcium bis-(2,4,6-trimethylbenzoylphenylphosphinate) (Compound 8)

15 parts by weight of the sodium salt of Example 1 were dissolved in 75 parts by weight of water, and 125 parts by volume of a 10% strength aqueous calcium chloride solution were added a little at a time to this solution. The resulting precipitate was filtered off under suction, washed with water and dried in a drying oven under reduced pressure at 50° C., and 14.7 parts by weight of product were obtained.

EXAMPLE 4

Methyldiethanolammonium 2,4,6-trimethylbenzoylphenylphosphinate (Compound 12)

5.8 parts by weight of 2,4,6-trimethylbenzoylphenylphosphinic acid were dissolved in 30 parts by volume of methylene chloride, and 2.4 parts by weight of methyldiethanolamine were added. After methylene chloride had been stripped off, the product was obtained.

EXAMPLE 5

To measure the hardening activity, the temperature curve for the unsaturated polyester resin (UP resin) was recorded during exposure to UV light. For this purpose, a temperature sensor coated with a layer of wax and connected to a temperature recorder (®Tastotherm Script 3N, standard sensor T 300 from Deutsche Gulton GmbH) was immersed in a tinplate lid which had a diameter of 5 cm and contained 10 g of UP resin as a 4.8 mm thick layer. To avoid heat losses during the exposure to UV light, the lid was embedded in rigid expanded polyurethane foam. The UV light source used comprised 5 fluorescent tubes (TLAK 40 W/05 from Philips) side by side, at a distance of 8.5 cm from the UP resin surface.

The hardening time $HT_{25°\ C.}-T_{max}$ and the maximum hardening temperature $T_{max}$ achieved were obtained, as characteristic parameters for the hardening activity, from the recorded temperature/time curves. The hardening time is the interval in which the sample temperature increases from 25° C. to $T_{max}$.

The Examples and Comparative Examples were carried out using the following unsaturated polyester resins:

Resin A was a 65% strength solution, in styrene, of an unsaturated polyester of maleic acid, o-phthalic acid, ethylene glycol and propylene 1,2-glycol in the molar ratio of 1:2:2.3:0.70, the solution being stabilized with 0.01% of hydroquinone. The unsaturated polyester had an acid number of 50.

Resin B was a 67% strength solution, in styrene, of an unsaturated polyester of maleic acid, tetrahydrophthalic acid and diethylene glycol in the molar ratio of 1:0.5:1.5, the solution being stabilized with 0.01% of hydroquinone. The unsaturated polyester had an acid number of 43.

Resin C was a 66% strength solution, in styrene, of an unsaturated polyester of maleic acid, o-phthalic acid and propylene 1,2-glycol in the molar ratio of 1:0.5:1.5, the solution being stabilized with 0.01% of hydroquinone. The unsaturated polyester had an acid number of 50.

The hardening activity of the novel compounds 1 to 16 (cf. Table 1) was compared with the properties of the following compounds:

I methyl 2,4,6-trimethybenzoylphenylphosphinate as described in U.S. Pat. No. 4,265,723, II isopropyl 2,4,6-trimethylbenzoylphenylphosphinate as described in U.S. Pat. No. 4,265,723, III benzil dimethyl ketal, and IV monosodium monomethylacetylphosphonate as described in European Published Application No. 9,348.

The results are summarized in Table 2, which shows that the novel compounds 4 to 18 are substantially more active hardeners than the prior art comparative compounds I to III. Table 2 also shows that the comparative compound IV, which is described in European Published Application No. 9,348 is unsuitable for photohardening.

TABLE 2

Hardening activity of various compounds

| Compound (0.2%) | Hardening activity of UP resins | | | | | |
|---|---|---|---|---|---|---|
| | A | | B | | C | |
| | $HT_{25°}$-$T_{max}$ (min/s) | $T_{max}$ (°C.) | $HT_{25°}$-$T_{max}$ (min/s) | $T_{max}$ (°C.) | $HT_{25°}$-$T_{max}$ (min/s) | $T_{max}$ (°C.) |
| I | 7/45 | 114 | 5/23 | 127 | 6/53 | 123 |
| II | 6/45 | 107 | 5/15 | 128 | 6/08 | 120 |
| III | 8/00 | 114 | 9/45 | 119 | 8/30 | 122 |
| IV | 13/15 | 30[(1)] | — | — | — | — |
| 4 | 5/53 | 117 | 4/37 | 125 | 5/23 | 122 |
| 5 | 5/38 | 118 | — | — | — | — |
| 6 | 5/53 | 115 | — | — | — | — |
| 8 | 5/53 | 114 | 6/00 | 130 | — | — |
| 9 | 5/53 | 110 | 4/45 | 125 | 5/45 | 129 |
| 11 | 5/23 | 118 | 4/30 | 124 | 5/15 | 120 |
| 12 | 6/15 | 116 | 5/08 | 129 | 5/23 | 123 |
| 13 | 6/08 | 115 | 5/30 | 126 | 5/23 | 121 |
| 14 | 5/30 | 122 | 4/53 | 118 | 5/38 | 123 |
| 15 | 7/15 | 113 | 8/00 | 119 | 7/30 | 109 |
| 16 | 5/15 | 115 | — | — | — | — |
| 17 | 5/38 | 120 | — | — | — | — |

[(1)] not hardened

EXAMPLE 6

To test the shelf life, 6.6 ml of each of the UP resins A, B and C (cf. Example 5) with an initiator content of 0.2% were introduced into brown sample bottles, and the closed bottles were stored at 60° C. At intervals of about 12 hours, the bottles were turned to determine whether gel particles had formed. As a measure of the shelf life, Table 3 gives the maximum storage time at which gel particles were still not observed.

In addition to the comparative compounds I, II and III, compound V below was also tested: V 2,4,6-trimethylbenzoyldiphenylphosphine oxide as described in U.S. Pat. No. 4,265,723.

The numbering scheme of the compounds in Table 3 is based on that of Table 1.

TABLE 3

Shelf life of UP resins containing a photoinitiator

| Compound | Shelf life (in hours) of the UP resins | | |
|---|---|---|---|
| | A | B | C |
| I | 180 | 155 | 180 |
| II | 140 | 155 | 120 |
| V | 140 | 140 | 120 |
| 4 | 190 | — | — |
| 9 | 180 | 140 | 180 |
| 11 | 180 | 155 | 204 |
| 14 | 180 | 155 | 204 |
| 17 | 270 | — | — |
| 18 | 270 | — | — |

Table 3 shows that the novel compounds 4, 9, 11, 14, 17 and 18 are substantially superior to the compounds II, III and V in respect of the shelf lives of the resins containing these compounds. Although the shelf lives of the resins containing 4, 9, 11 and 14 are not significantly different from those of the resins containing I, I is a substantially less active hardener than the novel compounds (see Example 5).

EXAMPLE 7

An unsaturated polyester was prepared by esterifying 143 parts of tetrahydrophthalic anhydride and 175 parts of maleic anhydride with 260 parts of diethylene glycol. 0.01% of hydroquinone was added, and thereafter a 64% strength solution of the polyester in styrene was prepared (solution D).

For the UV hardening experiments, 10 parts of styrene and 2 parts of the photoinitiator were added to 100 parts of solution D, and the finish was applied to photographic paper on a hardboard base by means of a film spreader (slotwidth 200 μm)

The film was dried in air for about 1 minute and then exposed to light from a 30 watt high pressure mercury vapor lamp of 1 cm arc length (Philips HTQ 7) located 15 cm above the object.

The hardening rate was determined by the König pendulum method (DIN 53,157), and is given in Table 4 together with the color measurements carried out on the hardened films.

The numbering scheme for the photoinitiators is based on that of Table 1 and Example 6.

TABLE 4

| Photoinitiator | Damping of pendulum after an exposure time of | | | | |
|---|---|---|---|---|---|
| | 5 s | 10 s | 15 s | 20 s | 25 s |
| V | 43 | 66 | 84 | 102 | 112 |
| 12 | 71 | 92 | 112 | 122 | 130 |

As shown in Table 4, compound 12 is a substantially more active hardener than the comparative compound V.

EXAMPLE 8

A monomer emulsion was prepared from 50 parts of methyl acrylate, 50 parts of ethyl acrylate, 1.3 parts of a 40% strength $C_{15}$-paraffin sulfonate, 1.3 parts of an adduct of isooctylphenol with 25 units of ethylene oxide (20% strength) and 210 parts of water in a conventional mixing unit.

This emulsion was introduced into a 1 l glass flask provided with an internal thermometer and a stirrer, and was freed from oxygen by twice evacuating the flask and gassing the emulsion with nitrogen. X parts of the photoinitiator in 6.7 parts of water were added, and the reaction vessel was then exposed for 60 minutes to light from a high pressure mercury vapor lamp of Type HQL/R 400 W from Osram, located 30 cm above the vessel. The beginning of polymerization was evident from an increase in the temperature. The amounts of photoinitiator employed and the properties of the resulting polymer dispersions are summarized in Table 5, photoinitiator 4 (cf. Table 1) being compared with photoinitiator VI (described in U.S. Pat. No. 4.257,859). For the same starting concentration, photoinitiator 4 gives a substantially lower content of residual monomers than that given by photoinitiator VI.

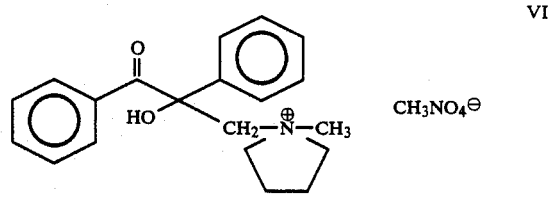

VI

Photoinitiator 4 permits photopolymerization even at very low starting concentrations, at which photoinitiator VI no longer initiates polymerization. Both results clearly show that photoinitiator 4 possesses a higher activity than photoinitiator VI, with the same K value of the resulting polymer dispersions.

TABLE 5

| Photo-initiator | Parts X employed | Solids content | Residual monomers | | Fikentscher K value |
| --- | --- | --- | --- | --- | --- |
| | | | Ethyl acrylate | Methyl acrylate | |
| 4 | 1.7 | 31.4 | <0.005% | 0.005% | 146.6 |
| VI | 1.7 | 30.8 | 0.012% | 0.036% | 146.1 |
| 4 | 0.04 | 31.3 | 0.019% | 0.051% | 156.8 |
| VI | 0.04 | | ← no polymerization → | | |

EXAMPLES 9 a TO c 294 parts of partially hydrolyzed polyvinyl acetate (degree of hydrolysis 82 mole %, average degree of polymerization 500) were dissolved in 294 parts of demineralized water at 90° C. by stirring the mixture for several hours. The solution was cooled to 70° C., and therafter 20 parts of 1,1,1-trimethylolpropane triacrylate, 1.0 part of 2,6-di-tert.-butyl-p-cresol and the amount of photoinitiator given in table 6, dissolved in 230 parts of 2-hydroxyethyl methacrylate, were added, with stirring. The homogeneous viscous solution was filtered, and dehydrated and degassed under reduced pressure. A 550 μm thick, nontacky layer was obtained by applying the solution onto steel sheet provided with an adhesive, and drying the layer for 24 hours at room temperature. The printing plate was pre-exposed for 2 seconds and thereafter exposed inagewise, through a negative, to light from a commercial 5 kW exposure unit for the times given in table 6. After washing out with water in a spray washer and drying at 100° C., the plate obtained possesses very good printing properties.

The thermal stability of the photosensitive solutions was determined by storing a sample in a closed ampoule at 80° C. In comparison with compound V, the novel photoinitiators improved the stability of the photosensitive mixture by a factor of 2 (see Table 6), with otherwise very similar behavior.

TABLE 6

| Example | Photoinitiator | Main exposure time | Stability |
| --- | --- | --- | --- |
| a | 4 parts of compound V | 30 sec. | 15 hours |
| b | 6 parts of compound 4 | 30 sec. | 34 hours |
| c | 7 parts of compound 12 | 35 sec. | 28 hours |

EXAMPLE 10

60 parts by weight of a 1:1:1 copolyamide consisting of PA-6, PA-6.6 and PA-6.13, 30 parts by weight of ethylene glycol bis-(N-methylolacrylamide) ether, 10 parts by weight of benzenesulfonic acid N-(n-butyl)-amide, 150 parts by weight of methanol, 20 parts by weight of water, 0.02 part by weight of a chromium complex dye (CI No. 12,195), 0.3 part by weight of potassium N-nitrosocyclohexylhydroxylamine and 2 parts by weight of the photoinitiator given in Table 7 were dissolved at about 70° C. The photopolymerizable material was brought to a solids content of about 65% by distilling off part of the solvent and was then cast, at 60° C., on to a strip of steel sheet provided with an adhesive, and drying was effected in a drying oven for about 2 hours at 80° C. The resulting photopolymerizable printing plate contained a 0.5 mm thick layer with a solids content of about 95%.

Using a test negative which had, inter alia, 54 screen lines, per centimeter, of 3% tonality, the plate was exposed to a UV light intensity of about 3,300 μW/cm² on a flat-plate exposure unit equipped with superactinic fluorescent tubes. The unexposed parts of the plate which were protected from the UV light by the opaque image elements of the negative were then washed out in a spray washer for 5 minutes at 30° C. and under a spray pressure of 5 bar, using an ethanol/water mixture containing 80% of ethanol. The plate was thereafter dried for 6 minutes at 110° C. The minimum exposure time required for faultless reproduction of the 3% tonality was measured, and the results for various photoinitiators are summarized in Table 7.

TABLE 7

| Initiator | Minimum exposure time required for reproducing the 3% tonality |
| --- | --- |
| 14 | 110 s |
| 4 | 115 s |
| III | 165 s |
| V | 190 s |

We claim:

1. An acylphosphine compound of the formula

where $R^1$ is $R^4$ or $OR^4$, $R^2$ is $-O^-M^+$, where $M^+$ is one equivalent of a cation, with an atomic weight of less than 138, of the main groups 1 to 3 of the Periodic Table, or the ammonium ion

where $R^8$ is hydrogen, $R^5$, $R^6$ and $R^7$ are identical or different and each is hydrogen or straight-chained or branched alkyl of up to 4 C atoms which is unsubstituted or substituted by a hydroxyl group, or is cyclohexyl, cyclopentyl, allyl, phenyl, β-acryloxyethyl or β-methacryloxyethyl or two of these substituents together with the nitrogen to which they are attached form morpholinium, $R^3$ is a substituted phenyl or naphthyl radical which carries $C_1-C_6$-alkyl, $C_1-C_6$-alkoxy, $C_1-C_6$-alkylthio, chloro or bromo substituents at least at the two positions ortho to the carbonyl group, $R^4$ is hydrogen or straight-chain or branched alkyl or alkenyl of up to 8 carbon atoms, which is unsubstituted or substituted by the group $-NR^5R^6$, or is phenyl, cyclohexyl or cyclopentyl, or phenyl which is monosubstituted or trisubstituted by straight-chain or branched alkyl, alkoxy, alkylthio groups of up to 6 carbon atoms, or $NR^5R^6$ wherein $R^5$ and $R^6$ have the above mentioned meaning or by halogen atoms having an atomic weight of up to 80, and X is oxygen.

2. An acylphosphine compound as claimed in claim 1, wherein $R^3$ is 2,6-dimethylphenyl, 2,4,6-trimethylphenyl, 2,3,6-trimethylphenyl, 2,6-dimethoxyphenyl, 2,6-dichlorophenyl, 2,6-bis-(methylthio)-phenyl, 2,3,5,6-tetramethylphenyl, 1,3-dimethylnaphth-2-yl or 1,3-dimethoxynaphth-2-yl.

3. An acylphosphine compound as claimed in claim 2, wherein $R^1$ is phenyl which is unsubstituted or mono-, di- or trisubstituted.

4. An acylphosphine compound as set forth in claim 1, wherein $R^1$ is phenyl, $R^2$ is $-O^-M^+$, where $M^+$ is one equivalent of a cation, with an atomic weight of less than 138, of the main groups 1 to 3 of the Periodic Table, $R^3$ is a methyl, methoxy, chloro or methyl thio substituted phenyl or naphthyl and X is O.

5. An acylphosphine compound as set forth in claim 2 wherein the ammonium ion is selected from the group consisting of ammonium, triethylammonium, tributylammonium, methyldiethanolammonium, anilinium, N,N-dimethylanilinium, β-acryloxyethyldiethylammonium, β-acryloxyethyldiethylammonium and N-(β-hydroxyethyl)-morpholinium.

6. An acylphosphine compound of the formula I as defined in claim 1, wherein $R^1$ is hydrogen, methyl, ethyl, isopropyl, n-butyl, sec.-butyl, isobutyl, t-butyl, amyl, n-hexyl, vinyl, 2-methylvinyl, prop-2-enyl, 2-dimethylaminoethyl, 3-dimethylaminopropyl, cyclohexyl, cyclopentyl, phenyl, halogen-substituted phenyl, $C_1$–$C_4$-alkyl substituted phenyl or $C_1$–$C_4$-alkoxy-substituted phenyl.

* * * * *